(12) United States Patent
Qu et al.

(10) Patent No.: US 7,094,395 B1
(45) Date of Patent: Aug. 22, 2006

(54) PIGMENT DISPERSION AND RELATED METHOD OF MANUFACTURE

(75) Inventors: Di Qu, Ada, MI (US); Jesse C. Leverett, Rockford, MI (US)

(73) Assignee: Access Business Group International LLC, Ada, MI (US)

( * ) Notice: Subject to any disclaimer, the term of this patent is extended or adjusted under 35 U.S.C. 154(b) by 480 days.

(21) Appl. No.: 10/132,818

(22) Filed: Apr. 25, 2002

(51) Int. Cl.
- A61K 9/107 (2006.01)
- A61K 7/021 (2006.01)
- B01F 17/00 (2006.01)
- B01F 3/12 (2006.01)

(52) U.S. Cl. .................... 424/63; 424/64; 424/400; 514/937; 514/938; 514/939; 514/943; 516/53; 516/75; 516/928

(58) Field of Classification Search ......... 514/937–39, 514/943, 937–38, 939; 516/53, 75, 928; 424/400, 63–4
See application file for complete search history.

(56) References Cited

U.S. PATENT DOCUMENTS

| | | | |
|---|---|---|---|
| 4,177,259 A * | 12/1979 | Barker et al. .......... | 424/63 |
| 4,857,307 A | 8/1989 | Suss et al. | |
| 5,066,485 A * | 11/1991 | Brieva et al. .......... | 424/63 |
| 5,196,186 A | 3/1993 | Omatsu et al. | |
| 5,260,052 A | 11/1993 | Peters et al. | |
| 5,340,582 A | 8/1994 | Sugasawa et al. | |
| 5,362,482 A | 11/1994 | Yoneyama et al. | |
| 5,486,233 A | 1/1996 | Mitchell et al. | |
| 5,486,354 A | 1/1996 | Defossez et al. | |
| 5,578,311 A | 11/1996 | Nagatani et al. | |
| 5,582,818 A | 12/1996 | Nakanishi et al. | |
| 5,599,533 A | 2/1997 | Stepniewski et al. | |
| 5,643,672 A | 7/1997 | Marchi et al. | |
| 5,897,868 A | 4/1999 | Kobayashi et al. | |
| 5,922,311 A | 7/1999 | Terren et al. | |
| 5,939,079 A | 8/1999 | Le Royer et al. | |
| 5,958,389 A | 9/1999 | Le Bras-Roulier et al. | |
| 5,980,921 A | 11/1999 | Biedermann et al. | |
| 6,004,567 A | 12/1999 | Marchi-Lemann et al. | |
| 6,132,745 A | 10/2000 | Marchi-Lemann et al. | |

* cited by examiner

*Primary Examiner*—Edward J. Webman
(74) *Attorney, Agent, or Firm*—Warner Norcross & Judd LLP

(57) ABSTRACT

A method for producing a colored cosmetic composition having inorganic pigments resistant to agglomeration in an oil-in-water emulsion. The method includes the following: preparing an oil dispersion by adding inorganic pigments directly to an oil; preparing an aqueous base that includes water; combining the oil dispersion and aqueous base; and partitioning the inorganic pigments between the oil and the aqueous phase under controlled conditions, for example, hydrophile-lipophile balance, agitation time and speed, and cooling rate. The present invention provides a process to easily disperse iron-oxide pigments, even black iron-oxide pigments, in oil-in-water emulsions. The present invention provides colored cosmetic compositions that have excellent properties, such as smoothness, adhesion to skin, uniform color, ease of removal, smudge resistance and non-oiliness.

24 Claims, No Drawings

PIGMENT DISPERSION AND RELATED METHOD OF MANUFACTURE

BACKGROUND OF THE INVENTION

This invention relates to a novel process for preparing metal oxide pigment dispersions. More particularly, this invention relates to pigment dispersions that are well-suited to color cosmetics.

Various cosmetic products, such as loose or compact powders, make-up foundations, blushes, eye shadows and lipsticks are colored using inorganic pigments dispersed in a carrier. Examples of these inorganic pigments are iron oxides, zinc oxide, talc, titanium dioxide, chromium hydroxide, and chromium oxide. The formed cosmetic products may be oil-in-water emulsions, water-in-oil emulsions or anhydrous compositions.

In general, cosmetics must (1) feel smooth and apply uniformly, (2) be easy to remove, (3) be hard to smudge and (4) be non-oily. Water or aqueous based cosmetics satisfy most of these requirements, usually in the form of oil-in-water emulsions. Oil-in-water emulsions are desirable because they have a pleasing skin-feel and texture. Moreover, they do not have the greasy feel of water-in-oil emulsions or the rough, dry, powdery feel of anhydrous cosmetic compositions.

Despite the desirable properties of oil-in-water emulsions, it is difficult to prepare these emulsions while maintaining even dispersion of inorganic pigments within the emulsions. This is because inorganic pigments, especially metal oxide pigments, tend to agglomerate. Specifically, the pigment particles attract to one another and form a colloid or enlarged clump of pigment when added directly to oil-in-water dispersions. If the pigments are not evenly dispersed, aesthetically unpleasing dark spots or swirls may appear in the final cosmetic. Further, the uneven dispersions or agglomeration of pigment particles creates an abrasive feel on the skin.

A variety of methods are used to enhance dispersion and prevent agglomeration of inorganic pigments. In all of these methods, the pigment particles are treated and directly added to the oil-in-water emulsion or the water phase of the oil-in-water emulsion to provide coloring. One method disclosed in U.S. Pat. No. 5,260,052 to Peters et al, coats inorganic pigments with polymers to promote even dispersion in a water base. Another method in U.S. Pat. No. 6,004,567 to Marchi-Lemann uses nano-pigment particles mixed with fillers and dispersed in a water base. Yet another method directly coats metal oxide pigments with a hydrophilic surfactant to increase its water dispersibility when added directly to an oil-in-water emulsion.

The above methods produce acceptable results for some inorganic pigments, but typically fail to evenly disperse metal oxide pigments in the emulsion. This problem is particularly acute when using black iron-oxide pigments. Due to their magnetic nature, iron-oxide pigments agglomerate even when they are treated with the methods above. Thus to keep the pigment particles evenly dispersed in the oil-in-water emulsion, high-speed shearing mixers are used. Even when such techniques are implemented, re-agglomeration may occur in holding tanks before the finished product is poured into retail sale packaging. To prevent this, many manufacturers add a second high-speed mixer to the holding tank. In some cases, however, a high-speed mixer over-agitates, whips or froths the product before it is poured into retail containers. Resulting froth or air bubbles can cause color changes, discoloration, air pockets and/or pigment particle agglomeration in the final product.

SUMMARY OF THE INVENTION

The aforementioned problems are overcome by the present invention wherein inorganic pigment particles are dispersed in an oil-in-water emulsion so that agglomeration of the pigment particles in the emulsion and any cosmetic manufactured from the emulsion is minimized. More specifically, the present invention is directed to a process of forming a cosmetic composition by dispersing metal-oxide pigment particles in an oil carrier and combining the resultant oil dispersion with an aqueous phase.

A preferred embodiment of the process of the present invention includes the following: preparing an oil dispersion by adding inorganic pigment to an oil; preparing an aqueous base that includes water; mixing the oil dispersion and aqueous base; and partitioning or distributing the pigments from the oil dispersion into the aqueous phase. Preferably, the oil dispersion includes homogeneously dispersed inorganic pigments that are selected to provide the desired coloration of the resultant cosmetic. It is believed that the preferred process prevents agglomeration of the inorganic pigment particles because the oil in the oil dispersion coats the inorganic particle and acts as a hydrophobic carrier. Accordingly, when the oil dispersion and aqueous phase are combined, the oil-coated pigment particles separate or partition into the aqueous phase with reduced potential to agglomerate with one another.

In another aspect of the invention, an emulsifier is used to enhance the partitioning of the pigments into the aqueous phase, specifically, the substantially uniform distribution of the pigments into the aqueous phase.

In a third aspect of the invention, the oil dispersion and aqueous phases are combined at a controlled rate with agitation.

The inventive process is advantageous because the resultant oil-in-water emulsion and subsequent cosmetic composition include non-agglomerated and well-dispersed inorganic pigment particles. As a result, the cosmetic has enhanced properties of smoothness, adhesion, ease of removal and smudge resistance. Moreover, when the cosmetic is applied to skin, it provides a uniform shade and/or color. Furthermore, the improved cosmetic may be manufactured without the use of secondary high-speed mixers to prevent the agglomeration of pigment particles during packaging.

These and other objects, advantages and features of the invention will be more fully understood and appreciated by reference to the detailed description of the preferred embodiments.

DETAILED DESCRIPTION OF THE INVENTION

The present invention is generally formed by mixing water or an aqueous base with an oil dispersion or oil mixture that contains pigments. The mixed aqueous base and oil mixture are agitated by shearing to form an oil-in-water emulsion in which the pigments are partitioned from the oil phase and into the aqueous phase. The term "pigment" as used herein means any natural or synthetic organic or inorganic substance that imparts a color, including black or white, to the final cosmetic formulation.

In the preferred embodiment, the cosmetic composition includes at least one pigment, oil, water, a humectant, a wax and/or a plasticizer, and an emulsifier. Other ingredients, such as moisturizers and preservatives, may be added as desired.

In the preferred embodiment, the pigments are first selected. The selection is based on the desired color of the resultant cosmetic. The pigments are conventional and may include inorganic materials such as titanium dioxide, iron oxides of various colors, including but not limited to yellow, red, and/or black iron oxides, zinc oxide, talc, chromium hydroxide, chromium oxide and any combination thereof. The pigments preferably are uncoated, but may be coated with polymers or other conventional coatings to change their surface properties. In the preferred embodiment, the pigments are substantially spherical and about 1 to about 10 microns in diameter. Other dimensioned pigments may be selected, provided those dimensions facilitate even dispersion of the pigments in oil. The pigment is at least about 0.1%, preferably at least about 2% and more preferably at least about 6% by weight of the cosmetic composition. Unless otherwise provided herein, all parts or percentages are percent of weight of the final product weight. The pigment may comprise up to 12%, preferably up to 10% and more preferably up to 8% by weight of the cosmetic composition. The total pigment content of the cosmetic composition may be further subdivided into specific pigments depending on the desired final color of the cosmetic.

The oils used in the present invention can be any water-immiscible solvent. Oils that may be used include but are not limited to castor oil, olive, oil, soybean oil, grape seed oil, sesame oil, maize oil, rapeseed oil, sunflower oil, cottonseed oil, avacodo oil, mink oil, turtle oil, groundnut oil, hydrocarbon oils, silicone oil, higher fatty acids, and higher fatty alcohols. In the preferred embodiment, castor oil is used because of the feel and texture it gives to the resultant cosmetic composition.

In another step of the preferred embodiment, the oil and pigments are mixed to form a pigment-in-oil dispersion or "oil dispersion." It is preferred that the only ingredients present in the oil dispersion are pigments(s) and the oil(s), e.g., no fillers present, to facilitate substantial and thorough cooling of the surfaces of pigment particles with the oil. Optionally, other ingredients may be present, however, the mixing of the oil, pigments and other ingredients may be altered to prevent agglomeration of pigment particles. The preferred pigment-in-oil dispersion contains a pigment-to-oil weight ratio of about one to one. Too much oil facilitates the processing and dispersion of the pigment, but makes the resultant cosmetic feel oily. Too little oil may prevent satisfactory dispersion of the pigments. Preferably, the resultant cosmetic composition contains about 4% to about 14% oil. Separate pigment-in-oil dispersions are prepared for each pigment. These pigment-in-oil dispersions are then agitated until they are somewhat lump-free and have an even consistency. Agitation is preferably carried out with a turbine agitator, for example, a Model NAR-33 turbine agitator with a R-100 type impeller commercially available from Lightnin of Rochester, N.Y., U.S.A.

In the preferred embodiment, each pigment-in-oil dispersion is milled to break apart clumps of pigments, or to further separate the pigments until a selected particle size criterion is met. To mill the pigment-in-oil dispersions, a conventional ball mill may be used. One example of such a ball mill is a CoBall mill Model MSM-12, which is commercially available from Fryma of Edison, N.J. U.S.A. The pigment-in-oil dispersion is passed through the CoBall mill until the major dimensions of pigment particles are less than under one one-thousandth of an inch (0.025 mm). Other particle sizes may also be used, provided that they evenly disperse and do not substantially re-agglomerate. In some cases it is unnecessary to mill the pigment particles, but most iron oxides, especially black iron-oxide pigments, must be milled to ensure an even dispersion and to prevent later agglomeration.

In another step of the preferred embodiment, the individual pigment-in-oil dispersions are combined and blended together to ensure color uniformity using conventional techniques.

In an alternative embodiment, each pigment-in-oil dispersion first may be combined with the other pigment-in-oil dispersions. This combined pigment-in-oil dispersion then may be milled until the particles are of the desired size.

In yet another step, the aqueous phase is formed. Preferable ingredients of the aqueous phase include: water, humectant, plasticizers, cosmetic base-forming wax and emulsifiers. Optionally, any of the above ingredients may serve a dual function, e.g., the humectant may also function as a plasticizer. The aqueous phase is formed in a large kettle, preferably large enough to accommodate the addition of the oil dispersion to form the oil-in-water emulsion within the kettle. The size of the kettle may vary depending on the desired batch size.

The kettle includes a high-shear mixer, such as a turbine agitator, although other agitators, stirrers or means of mixing may be used. In the preferred embodiment a flat-blade turbine agitator is used, however a pitched-blade turbine agitator may easily be substituted. An acceptable flat-blade turbine agitator is Model XJ-87AV with a R-100 type impeller, commercially available from Lightnin of Rochester, N.Y., U.S.A. The agitator ensures proper mixing of the ingredients of the aqueous phase in the kettle. The kettle is preferably cylindrical, with a diameter preferably about 5 times, more preferably about 2 to 4 times and most preferably about 2.5 to about 3.5 times the diameter of the mixing impeller of the agitator.

In a sub-step of forming the aqueous phase, water is added to the kettle. The water is preferably treated by distillation and/or reverse-osmosis. The water may be preheated to a temperature hot enough to soften or melt wax that may be added later. Alternatively, the water may be added at ambient temperature and later heated to a sufficient temperature to soften or melt the wax. Preferably, the water content of the resultant cosmetic composition is at least about 30% by weight, preferably at least about 38% or more preferably about 42%. The water content may be up to about 62%, preferably up to about 52%, and more preferably up to about 48%.

In another sub-step of forming the aqueous phase, humectant is added to the kettle. The humectant moisturizes a user's skin and prevents resultant cosmetics from feeling dry, thereby improving their aesthetic feel. Humectants include organic polyols, such as glycerin, propylene glycol, dipropylene glycol, butylene glycol, ethylene glycol, hexylene glycol and sugar alcohols such as sorbitol and mixtures thereof. Glycol is preferred because it provides a more satisfactory texture without the sticky or tacky feel common to glycerol. Preferred humectants are water-soluble. Preferred glycols are $C_1$–$C_{15}$ alkylene glycols, more preferred are $C_2$–$C_8$ alkylene glycols and most preferred are $C_3$–$C_5$ monomeric glycols.

When butylene glycol is used as a humectant, it may also serve as a plasticizer in the resultant cosmetic composition to assist cake formation by gelling the waxes and other components together. As will be appreciated, too much butylene glycol causes undesirable, rubbery cake formation, whereas too little butylene glycol causes brittle and crack-prone cake formation. Therefore, the proper amount of butylene glycol is desired to provide acceptable cake formation. This proper amount is based on experiment. In general, the humectant content of the resultant cosmetic composition is from about 8%, preferably from about 15%, and more preferably from about 23% to about 32%, preferably to about 27% and more preferably to about 25% by weight of the resultant cosmetic composition.

In another sub-step, a plasticizer is added to the aqueous phase. Acceptable plasticizers include any of the water-soluble plasticizers listed in McCutcheon's Functional Materials, VII, 1992 and any organopolysiloxanes. The plasticizer content of the resultant composition (excluding the glycol discussed above) is from about 0.5% by weight, preferably from about 5% and more preferably from about 7% to about 25% by weight, preferably to about 10% by weight and more preferably to about 20% by weight of the resultant cosmetic composition.

Organopolysiloxanes may be rendered water-soluble either by chemical modification, or physically by adding a surfactant. Organopolysiloxanes may be used alone or mixed in the aqueous phase. A particular chemically solubilized organopolysiloxane that may be used in the present invention is a copolymer of siloxane and hydrolyzed or unhydrolyzed protein, as described in EP-A-540,357 the disclosure of which is hereby incorporated by reference. Examples of such copolymers are the copolymers of polysiloxane or derivatives covalently linked (by grafting) to a protein, hydrolyzed or unhydrolyzed, such as casein, elastin, collagen, keratin, silk or a wheat or soya protein.

Other organopolysiloxanes that may be used in the cosmetic composition of the present invention are dimethicone copolyols and their derivatives. Dimethicone copolyols are provided by Dow Corning of Midland, Mich., U.S.A., and are reported in the publication "Water-soluble dimethicone copolyol waxes for personal care industry" by Linda Madore et al, pp. 1 to 3.

In yet another sub-step of forming the aqueous phase, a wax is added to provide texture, structure and a soft feel to the resultant cosmetic composition. Preferably, the aqueous phase is heated to the proper temperature so that the wax melts as it is added to the aqueous phase. This heating is preferably done before adding the wax to the aqueous phase. As will be appreciated, the wax also may act as a plasticizer, but is not included in the weight content of the plasticizer above. Preferably, the wax is water-soluble or non-water-soluble and modified so that it becomes water-soluble. The water-soluble wax may be natural or synthetic. Generally, any water-soluble wax that effectively carries pigment, i.e, the wax allows pigment to disperse consistently, is a wax contemplated by this invention. Preferably, Jojoba wax PEG-120 esters (International Nomenclature of Cosmetic Ingredients (INCI) Name) are used as the wax in the present invention. Jojoba wax PEG-120 ester is the polyethylene glycol derivative of the acids and alcohols obtained from the saponification of *Simmondsia chinensis* (Jojoba) oil (q.v.) with an average ethoxylation value of 120. Optionally, methoxy derivatives of water-soluble Jojoba wax PEG-5 may be substituted. Other waxes may be easily substituted. The amount of wax used is balanced in a ratio with glycol present in the aqueous phase. The resultant cosmetic composition includes a wax present in an amount by weight from about 3%, preferably from about 5%, more preferably from about 8% to about 15%, preferably to about 12%, and more preferably to about 10%.

In a further sub-step, an emulsifier is added to the aqueous phase to help the pigments partition from the oil dispersion into the aqueous phase in a uniform manner. Emulsifiers suitable for use in the present invention are metal salts of stearic acid, including but not limited to sodium stearate, titanium stearate, zinc stearate, magnesium stearate and potassium stearate. Preferred is sodium stearate. Other emulsifiers may be used as desired. The stearate used may act both as a wax to provide texture structure and a soft cake feel to the cosmetic product, however, the stearate content is not included in the percent weight content of the wax. The emulsifier is from about 3%, preferably from about 4% and more preferably from about 4.2% to about 15%, preferably to about 12%, and more preferably to about 8% by weight of the resultant cosmetic composition.

The metal salts of stearic acid act as a surface-active agent that helps incorporate oil within the water when the oil dispersion and aqueous phase are combined, as discussed below. The stearate helps set the appropriate environment for pigments to bridge the gap between the water and oil phase by controlling the rate at which the pigments partition between phases. If the stearate causes the pigments to move too fast between the oil dispersion and aqueous phase, re-agglomeration of the pigments may occur.

To move the inorganic pigments between the oil dispersion and aqueous phase at an acceptable rate, the emulsifier has or induces a Hydrophile-Lipophile Balance (HLB) value from a lower limit of at least about 14, preferably at least about 15 and more preferably at least about 16. The emulsifier has or induces an upper limit HLB value of preferably about 20 and more preferably about 16. If different waxes and oils are used, this HLB range of values may differ. The correct HLB value or range of values ensures that the pigment particles move from the oil dispersion to the aqueous phase without agglomerating into clumps or groups of particles. For example, if the HLB value is too low, the transfer of pigments from the oil dispersion to the aqueous phase will decrease. If the HLB value is too high, the oil may be stripped from the surface of pigment molecules, causing them to attract one another and agglomerate in the aqueous phase.

In an optional sub-step, a preservative or anti-bacterial agent, from about 0.1% to about 0.5% of the resultant composition may be added to the aqueous phase to prevent bacterial growth and preserve the cosmetic. A preferred preservative is methylparaben, which is present at about 0.3% in the cosmetic composition. Other preservatives, such as phenoxyethanol, benzyl alcohol, methylchloroisothiazolinone, methylisothiazolinone (trade name: Kathon CG), and chlorphenesin, or some combination thereof may be substituted in sufficient amounts. The cosmetic may also be made without a preservative.

In another optional sub-step, a powder, such as HDI/Trimethylol Hexyllactone Crosspolymer (INCI name), may be added to the aqueous phase to give the resultant cosmetic composition a smooth, silky feel. Such powders may also be added to act as anti-caking agents and/or a line-blurring agent and/or prevent the resultant cosmetic composition from becoming too dry or too hard. The amount of powder added affects the texture and other physical properties such as color and specific gravity. Examples of other powders that may be added are spherical silicas, polymethyl methacrylates, polyethylene, glass beads, and any particulate material that is able to diffuse light impinging on the skin. The particles of these powders are preferably spherical, but may be platelet in structure. HDI/Trimethylol Hexyllactone Crosspolymer is a cross-linked condensation polymer formed from the reaction of hexyldiisocyanate with the esterification product of trimethylolpropane with 6 to 7 moles of hexyllactone. The powder provides the proper texture and feel in the resultant cosmetic composition when at least about 0.1%, preferably at least about 0.5% and more preferably at least about 1% by weight. The powder in the resultant cosmetic composition is preferably not more than 4% and more preferably not more than 3% by weight.

After the aqueous phase is prepared, its temperature is preferably maintained within a range of about 60° C. to about 68° C. and more preferably in a range of about 60° C. to about 63° C. This range may vary depending on ingredients used, for example, the type of wax and type of oil.

In yet another step, after the oil dispersion and aqueous phase are prepared, they are combined in the kettle described above at a controlled and constant rate, which is experimentally determined. The rate of should be slow enough to prevent agglomeration, frothing, or anything else that may detract from the quality of the resultant cosmetic composition. As the oil dispersion and aqueous phase are combined, the resulting mixture is agitated, preferably under high-shear conditions.

In the preferred embodiment, the flat-blade turbine agitator described above, agitates the resulting mixture with a spinning tip speed of about 76 to 254 centimeters per second (cps). In the preferred embodiment, the tip speed has an upper limit of about 215 cps, preferably 206 cps and more preferably 191 cps, and a lower limit of about 88 cps, preferably 109 cps and more preferably 139 cps. Agitation continues preferably more than 50 minutes and more preferably about 60 to about 90 minutes, after the combination of the oil dispersion and aqueous phase.

Agitation is complete when the pigments partition from the dispersed oil phase into the continuous aqueous phase. Preferably, the pigments partition so that they are uniformly and/or homogeneously distributed throughout the aqueous phase. "Partition" means that in an oil dispersion/aqueous phase mixture, pigment particles migrate out from large masses of oil in the oil dispersion, i.e., the dispersed oil phase, with a thin coat of oil on the particles' outer surfaces, and distribute or disperse in the aqueous phase, i.e., the continuous phase. More specifically, each pigment particle, which is typically hydrophilic by itself, becomes partially lipophilic and partially hydrophilic when it is coated with a thin layer of oil in the disperse oil phase. When the disperse oil phase is mixed with an aqueous phase, this partially lipophilic and partially hydrophilic, oil-coated pigment particle is compatible with both the disperse phase, e.g., large droplets of oil, and the aqueous phase, e.g., water. Accordingly, such oil-coated particles disperse in both the disperse phase and aqueous phase with minimal or no distinct preference for either. Under a preferred Hydrophilic-Lipophilic Balance (HLB), for example an HLB greater than 14, which may be provided by emulsifiers, oil-coated pigment particles are urged to migrate out from the disperse phase and disperse in the aqueous phase.

An example of a partitioned pigment is a black iron oxide pigment particle, or a small group of several particles, that is substantially coated with castor oil, and dispersed out from large droplets of castor oil into the aqueous phase of an oil-in-water emulsion.

The duration of agitation depends on the ingredients, the rate of agitation, and the means of agitation. Typically, the rate of agitation must ensure good turnover of the oil dispersion and aqueous phase, while not aerating or frothing the mixture. During agitation, the batch preferably is cooled from about 63° C. to about 27° C. through two-stage cooling at controlled cooling rates. In a preferred embodiment, the first stage cools the batch from about 63° C. to about 45° C. The second stage cools the batch from about 45° C. to about 27° C. The cooling rate for the first stage is preferably from about 0.70° C. per minute to about 0.80° C. per minute, more preferably from about 0.72° C. per minute to about 0.78° C. per minute, and most preferably about 0.74° C. per minute to about 0.76° C. per minute. The cooling rate for the second stage is preferably from about 0.40° C. per minute to about 0.50° C. per minute, more preferably about 0.42° C. per minute to about 0.48° C. per minute and most preferably about 0.44° C. per minute to about 0.46° C. per minute.

The temperature and agitation induce the pigments to partition from the oil phase into the aqueous phase and form cosmetics of the desired shade. The shade of the cosmetic may be adjusted by adding amounts of each individual selected amounts of pigment-in-oil dispersion necessary to achieve the desired shade. These pigment-in-oil dispersions are of a pigment particle size of less than one one-thousandth of an inch (0.025 mm) and added to the batch as it is under agitation.

After agitation, the batch is allowed to cool to about 32° C. before being discharged into individual storage containers. This temperature may vary based on the ingredients. Given the partitioning of the pigment particles in the aqueous phase, those particles do not re-agglomerate, they are discharged into individual cosmetic storage containers. In the example that follows, all measurements are in percent by weight of the resultant cosmetic.

EXAMPLE

A cosmetic composition is prepared from a pigment-in-oil dispersion and an aqueous phase. The pigment-in-oil dispersion is formed by mixing the pigments in Table I with 8% castor oil.

TABLE I

Pigments of Example

| Pigment | Weight Percentage of Resultant Cosmetic Composition |
|---|---|
| Titanium dioxide | 6% |
| Yellow iron oxide | 1% |
| Red iron oxide | 0.5% |
| Black iron oxide | 0.5% |

Separately, an aqueous phase is prepared in a mixing kettle from the ingredients of Table II.

TABLE II

Aqueous Phase Ingredients of Example

| Ingredients | Weight Percentage of Resultant Cosmetic Composition |
|---|---|
| Water | 47.2% |
| Butylene Glycol | 22% |
| Jojoba wax PEG-80 | 9% |
| Sodium stearate | 4.5% |
| HDI/Trimethylol Hexyllactone Crosspolymer | 1% |
| Methylparaben | 0.3% |

The resultant aqueous phase is heated to and maintained at 60° C.–63° C. A XJ-87AV agitator from Lightnin mixes the ingredients of the aqueous phase with a tip speed of 1.0–1.8 m/sec until the ingredients are homogeneously dispersed and the content of the aqueous phase is uniform.

Next, the oil dispersion is added to the aqueous phase in the mixing kettle. The agitator mixes this mixture at a tip speed of 1.5–2.2 m/sec over 1–3 minutes. Thereafter, mixing continues for a total of about 55 minutes while cooling the mixture in a first stage from 60° C. to 45° C. at a cooling rate of 0.75° C./min., and then cooling the mixture in a second stage from 45° C. to 27° C. at a rate of 0.45° C./min.

After cooling, the homogenous cosmetic composition is discharged into bulk storage containers. The composition may be used for immediate packaging or stored in bulk at ambient conditions for future packaging. If stored in bulk, the composition will solidify, and eliminate pigment agglomeration and/or settling.

To package the bulk-stored composition in individual retail containers, the composition is heated to and maintained at about 57° C. to about 63° C. in a holding kettle of the container filler with moderate agitation. After the bulk content is fully melted, it is poured into packaging suitable for retail sale.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents. Except in the claims and the specific examples, or where otherwise expressly indicated, all numerical quantities in this description indicating amounts of material, reaction conditions, use conditions, and the like, are to be understood as modified by the word "about" in describing the broadest scope of the invention. Any reference to an item in the disclosure or to an element in the claim in the singular using the articles "a," "an," "the," or "said" is not to be construed as limiting the item or element to the singular unless expressly so stated.

The embodiments of the invention in which and exclusive property or privilege is claimed are defined as follows:

1. A method of producing an oil-in-water emulsion comprising:
   dispersing an inorganic pigment in a water immiscible solvent;
   preparing an aqueous phase including water, the aqueous phase separate from said inorganic pigment and said water immiscible solvent, the aqueous phase including at least one ingredient selected from the group consisting of sodium stearate, potassium stearate, titanium stearate, zinc stearate and magnesium stearate, the ingredient having an HLB of about 14 to about 20;
   combining said water immiscible solvent including the inorganic pigment with the aqueous phase to form an oil-in-water emulsion; and
   agitating the oil-in-water emulsion for a time sufficient to partition the inorganic pigment into the aqueous phase but prevent the inorganic pigment from agglomerating.

2. The method of claim 1 wherein the inorganic pigment is a metal oxide.

3. The method of claim 1 wherein the aqueous phase includes ingredients selected from the group consisting of plasticizers, humectants, and wax.

4. A method of producing an oil-in-water emulsion comprising:
   dispersing an inorganic pigment in a water immiscible solvent;
   preparing an aqueous phase including water, the aqueous phase separate from said inorganic pigment and said water immiscible solvent;
   combining said water immiscible solvent including the inorganic pigment with the aqueous phase to form an oil-in-water emulsion; and
   agitating the oil-in-water emulsion for a time sufficient to partition the inorganic pigment into the aqueous phase but prevent the inorganic pigment from agglomerating,
   wherein the aqueous phase includes an emulsifier selected from the group consisting of sodium stearate, potassium stearate, titanium stearate, zinc stearate and magnesium stearate.

5. The method of claim 1 wherein the emulsifier has an HLB value of about 16 to about 18.

6. The method of claim 3 comprising heating the aqueous phase to a temperature sufficient to melt the plasticizer.

7. A method of producing an oil-in-water emulsion comprising:
   dispersing an inorganic pigment in a water immiscible solvent;
   preparing an aqueous phase including water, the aqueous phase separate from said inorganic pigment and said water immiscible solvent;
   combining said water immiscible solvent including the inorganic pigment with the aqueous phase to form an oil-in-water emulsion;
   agitating the oil-in-water emulsion for a time sufficient to partition the inorganic pigment into the aqueous phase but prevent the inorganic pigment from agglomerating;
   wherein the aqueous phase include an emulsifier having a HLB value of about 14 to about 20; and
   wherein the aqueous phase is heated to about 54° C. to about 63° C.

8. A method of producing an oil-in-water emulsion comprising:
   dispersing an inorganic pigment in a water immiscible solvent;
   preparing an aqueous phase including water, the aqueous phase separate from said inorganic pigment and said water immiscible solvent;
   combining said water immiscible solvent including the inorganic pigment with the aqueous phase to form an oil-in-water emulsion;
   agitating the oil-in-water emulsion for a time sufficient to partition the inorganic pigment into the aqueous phase but prevent the inorganic pigment from agglomerating; and
   cooling said oil-in-water emulsion in multiple stages wherein each stage has a different rate of cooling.

9. The method of claim 8 wherein said cooling comprises:
   a first stage of cooling the oil-in-water emulsion to a temperature below about 46° C. at a first cooling rate; and
   a second stage of cooling of the oil-in-water emulsion to a temperature below 30° C. at a second cooling rate.

10. The method of claim 9 wherein said first cooling rate is from about 0.7° C. per minute to about 0.8° C. per minute.

11. The method of claim 9 wherein said second cooling rate is from about 0.4° C. to about 0.5° C. per minute.

12. The method of claim 1 wherein said water immiscible solvent is selected from the group consisting of castor oil, olive, oil, soybean oil, grape seed oil, sesame oil, maize oil, rapeseed oil, sunflower oil, cottonseed oil, avacodo oil, mink oil, turtle oil, groundnut oil, hydrocarbon oils, silicone oil, higher fatty acids, and higher fatty alcohols.

13. A method of forming a cosmetic foundation comprising: preparing an oil dispersion including an oil and a pigment;

preparing a separate aqueous phase including an emulsifier, a humectant and a plasticizer, the emulsifier being at least one of sodium stearate, potassium stearate, titanium stearate, zinc stearate and magnesium stearate having an HLB value of about 14 to about 20;

adding the oil dispersion to the aqueous phase to form a mixture;

partitioning the pigment so that the pigment uniformly disperses in the mixture; and cooling the mixture at a rate sufficient to prevent agglomeration of the pigment in the mixture.

14. The method of claim 13 wherein the emulsifier is of a pre-selected HLB value sufficient to prevent agglomeration of the pigment dispersed in the mixture.

15. The method of claim 13 wherein the emulsifier has an HLB value of from about 16 to about 18.

16. The method of claim 13 wherein said pigment is an iron oxide pigment.

17. A method of forming a cosmetic foundation comprising:

preparing an oil dispersion including an oil and a pigment;

preparing a separate aqueous phase including an emulsifier, a humectant and a plasticizer;

adding the oil dispersion to the aqueous phase to form an oil-in-water emulsion mixture;

partitioning the pigment so that the pigment uniformly disperses in the mixture; and cooling the mixture at a rate sufficient to prevent agglomeration of the pigment in the mixture, wherein the emulsifier is a metal salt of stearic acid.

18. The method of claim 15 wherein the emulsifier is sodium stearate.

19. A method of forming a cosmetic foundation comprising:

preparing an oil dispersion including an oil and a pigment;

preparing a separate aqueous phase including an emulsifier, a humectant and a plasticizer;

adding the oil dispersion to the aqueous phase to form an oil-in-water emulsion mixture;

partitioning the pigment so that the pigment uniformly disperses in the mixture;

cooling the mixture at a rate sufficient to prevent agglomeration of the pigment in the mixture; and heating the aqueous phase to a temperature from about 35° C. to about 63° C.

20. The method of claim 13 wherein oil is selected from a group consisting of castor oil, olive, oil, soybean oil, grape seed oil, sesame oil, maize oil, rapeseed oil, sunflower oil, cottonseed oil, avacodo oil, mink oil, turtle oil, groundnut oil, hydrocarbon oils, silicone oil, higher fatty acids, and higher fatty alcohols.

21. The method of claim 13 wherein the humectant is a glycol selected from the group consisting of propylene glycol, butylene glycol, ethylene glycol and hexylene glycol.

22. A method of forming a cosmetic foundation comprising:

preparing an oil dispersion including an oil and a pigment;

preparing a separate aqueous phase including an emulsifier, a humectant and a plasticizer;

adding the oil dispersion to the aqueous phase to form an oil-in-water emulsion mixture;

partitioning the pigment so that the pigment uniformly disperses in the mixture; and cooling the mixture at a rate sufficient to prevent agglomeration of the pigment in the mixture, wherein said partitioning comprises:

heating the mixture from about 27° C. to about 63° C.; and agitating the mixture with a high-shear mixer.

23. A method of forming a cosmetic foundation comprising:

preparing an oil dispersion including an oil and a pigment;

preparing a separate aqueous phase including an emulsifier, a humectant and a plasticizer;

adding the oil dispersion to the aqueous phase to form an oil-in-water emulsion mixture;

partitioning the pigment so that the pigment uniformly disperses in the mixture; and cooling the mixture at a rate sufficient to prevent agglomeration of the pigment in the mixture, wherein said preparing an oil dispersion comprises:

adding the pigment particles to an oil;

agitating the oil; and milling the oil and pigment particles so that the major dimension of a majority of pigment particles is less than about 0.025 millimeters.

24. A method of forming a cosmetic foundation comprising:

preparing an oil dispersion including an oil and a pigment;

preparing a separate aqueous phase including a humectant, a plasticizer, and an emulsifier;

adding the oil dispersion to the aqueous phase to form a mixture; and partitioning the pigment so that the pigment uniformly disperses in the aqueous phase, wherein the emulsifier is selected from the group consisting of sodium stearate, potassium stearate, titanium stearate, zinc stearate and magnesium stearate, wherein the emulsifier has an HLB value sufficient to prevent agglomeration of the pigment when the pigment is dispersed in the aqueous phase.

* * * * *